US006296936B1

(12) United States Patent
Yahiaoui et al.

(10) Patent No.: US 6,296,936 B1
(45) Date of Patent: Oct. 2, 2001

(54) COFORM MATERIAL HAVING IMPROVED FLUID HANDLING AND METHOD FOR PRODUCING

(75) Inventors: Ali Yahiaoui, Roswell; Charles Edward Bolian, II, Buford, both of GA (US); Daryl Steven Bell, Neenah, WI (US); Nancy Ann Secen, Maumelle, AR (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/016,813

(22) Filed: Jan. 30, 1998

Related U.S. Application Data

(63) Continuation-in-part of application No. 08/898,188, filed on Jul. 22, 1997, now Pat. No. 6,028,016
(60) Provisional application No. 06/025,621, filed on Sep. 4, 1996.

(51) Int. Cl.[7] .................................................. D02G 3/00
(52) U.S. Cl. .......................... 428/378; 428/375; 428/393; 428/394
(58) Field of Search ................................... 428/375, 378, 428/393, 394

(56) References Cited

U.S. PATENT DOCUMENTS

| Re. 35,621 | 10/1997 | Schmalz ............... 156/308.8 |
|---|---|---|
| 3,338,992 | 8/1967 | Kinney . |
| 3,341,394 | 9/1967 | Kinney . |
| 3,485,706 | 12/1969 | Evans ...................... 161/72 |
| 3,502,538 | 3/1970 | Petersen . |
| 3,502,763 | 3/1970 | Hartmann . |
| 3,542,615 | 11/1970 | Dobo et al. . |
| 3,598,865 | 8/1971 | Lew . |
| 3,692,618 | 9/1972 | Dorschner et al. . |
| 3,802,817 | 4/1974 | Matsuki et al. . |
| 3,844,865 | 10/1974 | Elton et al. . |
| 3,849,241 | 11/1974 | Butin et al. . |
| 3,850,819 | 11/1974 | Shay ................... 252/8.75 |
| 3,855,046 | 12/1974 | Hansen et al. . |
| 3,891,008 | 6/1975 | D'Entremont . |
| 3,896,807 | 7/1975 | Buchalter ............. 128/261 |

(List continued on next page.)

FOREIGN PATENT DOCUMENTS

| 41 36 540 | 5/1992 | (DE) .............. A61F/13/15 |
|---|---|---|
| 099 428 | 2/1984 | (EP) . |
| 598204 | 5/1994 | (EP) .......... D06M/13/224 |
| 0712892 | 5/1996 | (EP) . |
| 01 104700 | 4/1989 | (JP) .............. A61K/7/00 |
| 9527005 | 10/1995 | (WO) . |
| 97/02376 | 1/1997 | (WO) . |
| 97/15651 | 5/1997 | (WO) .............. C11D/3/00 |
| 98/10134 | 3/1998 | (WO) .......... D06M/15/03 |

OTHER PUBLICATIONS

Manson, John A. and Sperling, Leslie H., *Polymer Blends & Composites*, Plenum Press, a divsion of Plenum Publishing Corp., New York, New York, pp. 273–277 (1976). No Month.

(List continued on next page.)

*Primary Examiner*—Cynthia H. Kelly
*Assistant Examiner*—J. M. Gray
(74) *Attorney, Agent, or Firm*—Pauley Petersen Kinne & Fejer

(57) ABSTRACT

An improved coform material having a plurality of synthetic fibers, a plurality of natural fibers commingled with the plurality of synthetic fibers and a treatment system including a surfactant selected from the group consisting of ethoxylated hydrogenated fatty oils, monosaccharides, monosaccharide derivatives, polysaccharides, polysaccharide derivatives, and combinations thereof, applied to the synthetic fibers. The integrated composite material is particularly suitable for use in personal care absorbent articles such as feminine hygiene products, diapers, training pants, absorbent underpants, and adult incontinence products.

16 Claims, 2 Drawing Sheets

U.S. PATENT DOCUMENTS

| | | | |
|---|---|---|---|
| 3,901,236 | 8/1975 | Assarsson et al. | 128/284 |
| 3,951,945 | 4/1976 | Heesen et al. . | |
| 3,966,918 | 6/1976 | Kawamata et al. . | |
| 4,011,389 * | 3/1977 | Langdon | 162/175 |
| 4,041,203 | 8/1977 | Brock et al. . | |
| 4,075,290 | 2/1978 | Denzel et al. . | |
| 4,076,633 | 2/1978 | Edwards et al. | 252/8.75 |
| 4,100,324 | 7/1978 | Anderson et al. . | |
| 4,110,227 | 8/1978 | Newkirk et al. | 252/8.9 |
| 4,125,662 | 11/1978 | Weiner et al. . | |
| 4,142,017 | 2/1979 | Blackburn et al. | 428/284 |
| 4,169,910 | 10/1979 | Graboski . | |
| 4,189,395 | 2/1980 | Bland | 252/91 |
| 4,192,754 | 3/1980 | Marshall et al. | 252/8.8 |
| 4,199,464 | 4/1980 | Cambre | 252/91 |
| 4,199,465 | 4/1980 | Rodriguez | 252/91 |
| 4,223,065 | 9/1980 | Amemiya et al. | 428/272 |
| 4,250,047 | 2/1981 | Katabe et al. | 252/49.5 |
| 4,275,120 | 6/1981 | Weiner . | |
| 4,283,292 | 8/1981 | Marshall et al. | 252/8.8 |
| 4,286,082 | 8/1981 | Tsubakimoto et al. | 526/240 |
| 4,291,092 | 9/1981 | Weiner . | |
| 4,297,408 | 10/1981 | Stead et al. . | |
| 4,317,736 | 3/1982 | Marshall | 252/8.75 |
| 4,339,494 | 7/1982 | Weiner . | |
| 4,340,382 | 7/1982 | Morlino et al. | 8/137 |
| 4,340,563 | 7/1982 | Appel et al. . | |
| 4,374,888 | 2/1983 | Bornslaeger . | |
| 4,410,447 | 10/1983 | Decker et al. | 252/351 |
| 4,413,032 | 11/1983 | Hartmann et al. . | |
| 4,416,787 | 11/1983 | Marshall et al. | 252/8.8 |
| 4,460,644 | 7/1984 | Pavlich . | |
| 4,536,324 | 8/1985 | Fujiwara et al. | 252/311 |
| 4,622,038 | 11/1986 | Login et al. | 8/115.6 |
| 4,627,931 | 12/1986 | Malik . | |
| 4,631,226 | 12/1986 | Jellinek | 428/270 |
| 4,672,091 | 6/1987 | Berta . | |
| 4,725,489 | 2/1988 | Jones et al. | 428/289 |
| 4,753,844 | 6/1988 | Jones et al. . | |
| 4,764,505 | 8/1988 | Fujinuma et al. . | |
| 4,789,588 | 12/1988 | Suzuki et al. . | |
| 4,791,144 | 12/1988 | Nagou et al. . | |
| 4,818,464 | 4/1989 | Lau . | |
| 4,878,974 | 11/1989 | Kagawa . | |
| 4,895,622 | 1/1990 | Barnett et al. . | |
| 4,938,888 | 7/1990 | Kiefer et al. | 252/91 |
| 4,959,396 | 9/1990 | Yankov et al. . | |
| 4,975,469 | 12/1990 | Jacoby et al. . | |
| 4,995,884 | 2/1991 | Ross et al. . | |
| 5,045,387 | 9/1991 | Schmalz . | |
| 5,057,361 | 10/1991 | Sayovitz et al. . | |
| 5,108,820 | 4/1992 | Kaneko et al. . | |
| 5,108,827 | 4/1992 | Gessner . | |
| 5,109,127 | 4/1992 | Sekiguchi et al. . | |
| 5,154,855 | 10/1992 | Sekiguchi et al. . | |
| 5,169,706 | 12/1992 | Collier, IV et al. . | |
| 5,169,712 | 12/1992 | Tapp . | |
| 5,176,953 | 1/1993 | Jacoby et al. . | |
| 5,190,747 | 3/1993 | Sekiguchi et al. . | |
| 5,236,963 | 8/1993 | Jacoby et al. . | |
| 5,238,586 | 8/1993 | Uphues et al. . | |
| 5,258,221 | 11/1993 | Meirowitz et al. . | |
| 5,266,392 | 11/1993 | Land et al. . | |
| 5,268,126 | 12/1993 | Balzer | 252/312 |
| 5,272,326 | 12/1993 | Fujita et al. . | |
| 5,310,730 | 5/1994 | Fujinuma et al. . | |
| 5,317,035 | 5/1994 | Jacoby et al. . | |
| 5,322,728 | 6/1994 | Davey et al. . | |
| 5,334,286 * | 8/1994 | Van Phan et al. | 162/158 |
| 5,336,552 | 8/1994 | Strack et al. . | |
| 5,342,534 | 8/1994 | Skrobala et al. . | |
| 5,362,497 | 11/1994 | Yamada et al. . | |
| 5,373,044 | 12/1994 | Adams et al. . | |
| 5,382,400 | 1/1995 | Pike et al. . | |
| 5,397,507 | 3/1995 | Bauer et al. | 252/549 |
| 5,446,100 | 8/1995 | Durrance et al. . | |
| 5,456,982 | 10/1995 | Hansen et al. . | |
| 5,468,797 | 11/1995 | Adams et al. . | |
| 5,474,776 | 12/1995 | Koyanagi et al. . | |
| 5,501,813 | 3/1996 | Fiischer et al. . | |
| 5,540,953 | 7/1996 | Harrington | 427/383.5 |
| 5,540,979 | 7/1996 | Yahiaoui et al. . | |
| 5,545,481 | 8/1996 | Harrington | 428/378 |
| 5,550,189 | 8/1996 | Qin et al. . | |
| 5,562,848 | 10/1996 | Wofford et al. | 252/8.84 |
| 5,567,808 | 10/1996 | Desai et al. . | |
| 5,571,619 | 11/1996 | McAlpin et al. . | |
| 5,582,904 | 12/1996 | Harrington . | |
| 5,594,070 | 1/1997 | Jacoby et al. . | |
| 5,595,675 | 1/1997 | Aso et al. | 252/8.61 |
| 5,605,651 | 2/1997 | Balzer . | |
| 5,605,683 | 2/1997 | Desai et al. . | |
| 5,620,788 | 4/1997 | Garavaglia et al. | 442/118 |
| 5,639,450 | 6/1997 | Oldenhove de Guertechin | 424/70.19 |
| 5,643,498 | 7/1997 | Li et al. | 252/357 |
| 5,643,588 * | 7/1997 | Roe et al. | 424/402 |
| 5,643,864 | 7/1997 | Li et al. | 510/499 |
| 5,652,048 | 7/1997 | Haynes et al. . | |
| 5,656,586 | 8/1997 | Li et al. | 510/535 |
| 5,667,749 | 9/1997 | Lau et al. . | |
| 5,700,331 | 12/1997 | Thomas et al. . | |
| 5,710,121 | 1/1998 | Tracey et al. | 510/467 |
| 5,711,994 | 1/1998 | Powers | 427/255.6 |
| 5,721,048 | 2/1998 | Schmalz | 428/369 |
| 5,756,112 | 5/1998 | Mackey | 424/402 |
| 5,759,926 | 6/1998 | Pike et al. | 442/333 |
| 5,763,334 | 6/1998 | Gupta et al. | 442/360 |
| 5,945,175 * | 8/1999 | Yahiaoui et al. | 427/534 |
| 6,017,832 * | 1/2000 | Yahiaoui et al. | 442/118 |
| 6,028,016 * | 2/2000 | Yahiaoui et al. | 442/118 |

OTHER PUBLICATIONS

Rodgers, J.E., Wide Line Nuclear Magnetic Resonance in Measurements of Finish–on–Fiber of Textile Products, Spectroscopy, 9(8), 40 (1994) No Month.

ICI Americas Inc. Technical Bulletin, *Ahcovel Base N–62 Liquid Nonionic Textile Softener*, 1978. No Month.

Chemical Abstract No. 124:185108, abstract of an article by Foerster et al., entitled Physicochemical properties of alkyl polyglycosides in personal care products, Parfuem. Kosmet. (1995), 76 (12). No Month.

* cited by examiner

COFORM MATERIAL HAVING IMPROVED FLUID HANDLING AND METHOD FOR PRODUCING

This application is a continuation-in-part of U.S. patent application Ser. No. 08/898,188, filed Jul. 22, 1997, now U.S. Pat. No. 6,028,016 the disclosure of which is incorporated herein by reference. The parent application claims priority from U.S. Provisional Application No. 06/025,621, filed Sep. 4, 1996.

BACKGROUND OF THE INVENTION

1. Field of the Invention

This invention relates to a coform material having improved fluid handling characteristics suitable for use in disposable personal care absorbent articles such as feminine hygiene products. Improved fluid handling is achieved by application of a surfactant treatment system which imparts an enhanced fluid intake rate on multiple insults and a significantly durable hydrophilic character.

2. Description of Prior Art

Absorbent personal care articles such as sanitary napkins, disposable diapers, incontinent-care pads and the like are widely used, and much effort has been made to improve the effectiveness and functionality of these articles. These articles generally include a liquid absorbent material backed by a liquid-impervious barrier sheet. To enhance the sense of comfort, the absorbent material has a facing of a material which masks at least the body-facing surface of the product. This cover material not only contains the absorbent material but also protects the wearer from continuous direct contact with moisture from previously wetted absorbent material. The cover material is typically a relatively low basis weight nonwoven fabric.

The production of nonwoven fabrics has long used meltblown, coform and other techniques to produce webs for use in forming a wide variety of products. Coform nonwoven fabrics are produced by combining separate polymer and additive streams into a single deposition stream in forming the nonwoven webs. Such a process is taught, for example, by U.S. Pat. No. 4,100,324 to Anderson et al. which is hereby incorporated by reference. U.S. Pat. No. 4,818,464 to Lau discloses the introduction of superabsorbent material as well as pulp, cellulose, or staple fibers through a centralized chute in an extrusion die for combination with resin fibers in a nonwoven web. The pulp, staple fibers, or other material are added to vary the characteristics of the resulting web, for example, strength and absorbency.

FIG. 1 is a partially schematic side elevation, partially in section, of a prior art method and apparatus for producing coform nonwoven fabrics. Basically, the method of formation of the coform nonwoven web involves extruding a molten polymeric material through a die head 11 into fine streams and attenuating the streams by converging flows of high velocity, heated gas (usually air) supplied from nozzles 12 and 13 to break the polymer streams into discontinuous microfibers of small diameter. The die head preferably includes at least one straight row of extrusion apertures. In general, the resulting microfibers have an average fiber diameter of up to only about 10 microns with very few, if any, of the microfibers exceeding 10 microns in diameter. The average diameter of the microfibers is usually greater than about one micron, and is preferably within the range of about 2–6 microns, averaging about 5 microns. While the microfibers are predominately discontinuous, they generally have a length exceeding that normally associated with staple fibers.

The primary gas stream 10 is merged with a secondary gas stream 14 containing individualized wood pulp fibers so as to integrate the two different fibrous materials in a single step. The individualized wood pulp fibers typically have a length of about 0.5 to 10 millimeters and a length–2-maximum width ratio of about 10/1:400/1. A typical cross-section has an irregular width of 30 microns and a thickness of 5 microns. The integrated air stream is then directed onto a forming surface to air form the nonwoven fabric. In the configuration shown in FIG. 1, the secondary gas stream 14 is formed by a pulp sheet divellicating apparatus comprising a picker row 20 having picking teeth for divellicating pulp sheets 21 into individual fibers. The pulp sheets 21 are fed radially, that is, along a picker row radius, to the picker row 20 by means of rows 22. As the teeth on the picker row 20 divellicate the pulp sheets 21 into individual fibers, the resulting separated fibers are conveyed downwardly toward the primary air stream through a forming nozzle or duct 23. A housing 24 encloses the picker row 20 and provides a passage 25 between the housing 24 and the picker row surface. Process air is supplied to the picker row in the passage 25 by means of duct 26 in sufficient quantity to serve as a medium for conveying the fibers through the forming duct 23 at a velocity approaching that of the picker teeth. The air may be supplied by any conventional means as, for example, a blower.

To convert the fiber blend in the integrated stream 15 into an integral fibrous mat or web, the stream 15 is passed into the nip of a pair of vacuum rolls 30 and 31 having foraminous surfaces that rotate continuously over a pair of thick vacuum nozzles 32 and 33. As the integrated stream 15 enters the nip of the rolls 30 and 31, the carrying gas is sucked into the two vacuum nozzles 32 and 33 while the fiber blend is supported and slightly compressed by the opposed surfaces of the two rolls 30 and 31. This forms an integrated, self-supporting fibrous web 34 that has sufficient integrity to permit it to be withdrawn from the vacuum roll nip and conveyed to a windup roll 35.

In order to satisfy the requirements for immediate transfer of each liquid application or insult through the cover material of feminine hygiene products as discussed hereinabove, it is necessary that the surfaces of the cover material or the surface of the fibers forming the nonwoven fabrics be first wetted by the liquid. Wettability of nonwoven webs or fibers thereof is known to be achievable by treating the surface thereof with surfactants. See, for example, U.S. Pat. Nos. 4,413,032 to Hartmann et al. and 5,045,387 to Schmalz. Alternative methods of imparting wettability to such materials are taught, for example, by U.S. Pat. No. 5,456,982 to Hansen et al. in which the bicomponent fibers are provided with permanent hydrophilic surface properties by incorporating a surface active agent into the sheath component and optionally by including a hydrophilic polymer or copolymer in the sheath component. See also, U.S. Pat. No. 5,582,904 to Harrington which teaches the incorporation into a polyolefin-containing cast or spin-melt composition for production of nonwoven materials a modifier composition comprising at least one M,M-polyalkoxylate 10–22 carbon fatty acid amine, inclusive of amines having 12–20 carbons and preferably 18 carbon linear straight chain moiety corresponding to that found in stearic or oleic acid, and up to about 60%, including 0.1%–45% by weight of a modifier composition, of a primary or a secondary 10–22 carbon fatty acid amide, such as stearamide.

SUMMARY OF THE INVENTION

It is one object of this invention to provide a coform material suitable for use in personal care absorbent articles having improved fluid handling performance over known materials. By improved fluid handling performance, we mean a material having enhanced fluid intake rates even after multiple insults and a significantly durable hydrophilic character.

This and other objects of this invention are achieved by an integrated composite material (coform, nonwoven fabric) comprising a plurality of synthetic fibers, a plurality of natural fibers commingled with the plurality of synthetic fibers, and a surfactant treatment system comprising a compound selected from the group consisting of ethoxylated hydrogenated fatty oils, monosaccharides, monosaccharide derivatives, polysaccharides, polysaccharide derivatives, and combinations thereof, applied to the plurality of synthetic fibers. These synthetic fibers are preferably polypropylene meltblown fibers and the natural fibers are preferably pulp fibers. In the integrated composite structure of this invention, the pulp fibers are commingled and/or entrapped by the polypropylene meltblown fibers. Although it is required that the surfactant be applied to the synthetic fibers, in accordance with a particularly preferred embodiment of this invention, both the synthetic and natural fibers are coated with the surfactant treatment system.

The integrated composite materials of this invention are suitable for use in limited use or disposable items, that is products and/or components used only a small number of times, or possibly only once, before being discarded. Examples of such products include, but are not limited to, personal care absorbent products such as sanitary napkins, diapers, training pants, incontinence garments, bandages, wipes and the like.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Definitions

Figure 1:
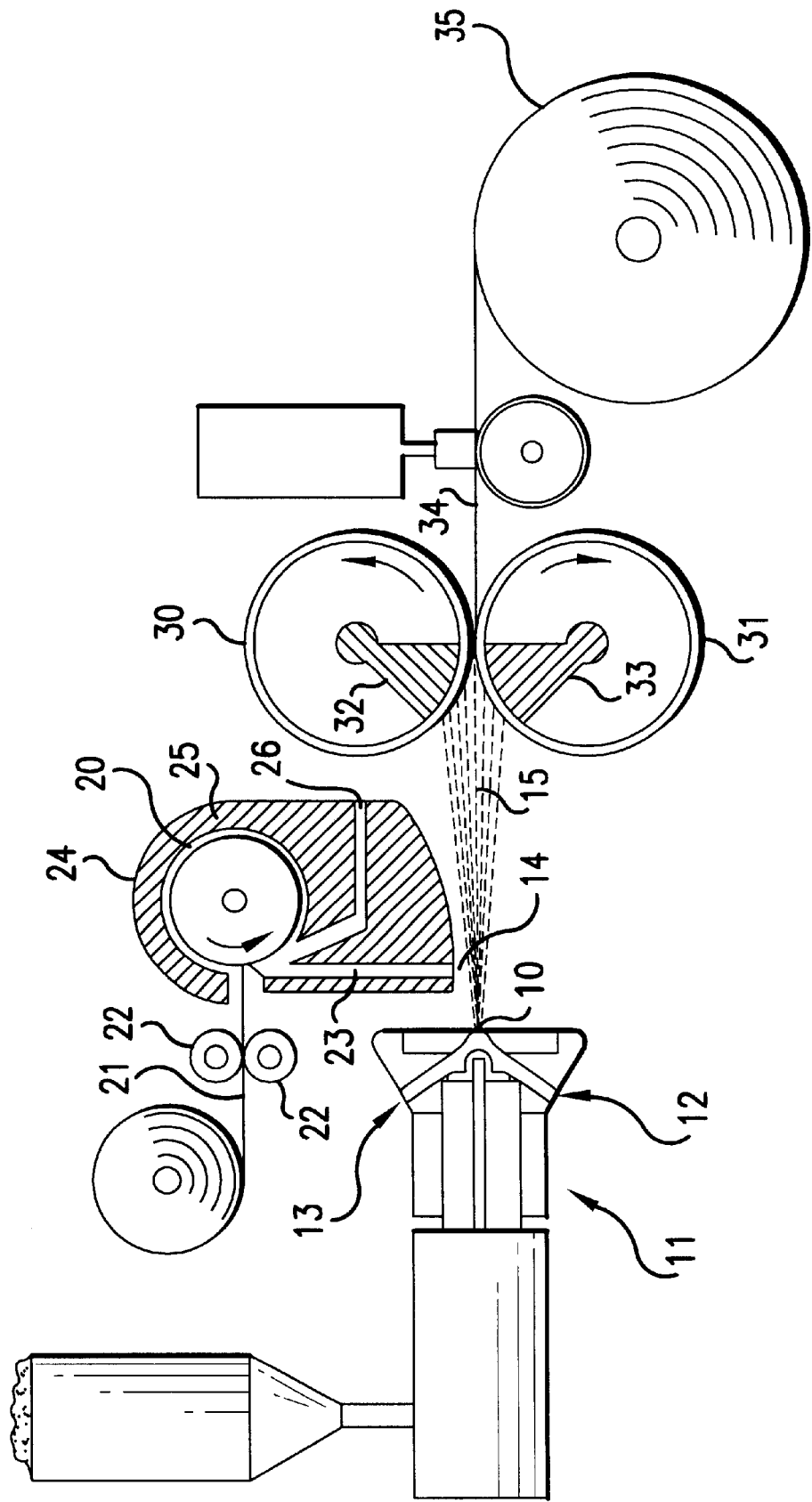
FIG. 1 is a partially schematic side elevation, partially in section, of a method and apparatus for producing coform nonwoven fabrics.

As used herein, the term "nonwoven fabric or web" means a web having a structure of individual fibers or threads which are interlaid, but not in a regular or identifiable manner, as in a knitted fabric. It also includes foams and films that have been fibrillated, apertured or otherwise treated to impart fabric-like properties. Nonwoven fabrics or webs have been formed from many processes such as, for example, meltblowing processes, spunbonding processes, and bonded carded web processes. Of particular interest in this invention are nonwoven fabrics produced by coform processes. The basis weight of nonwoven fabrics is usually expressed in ounces of material per square yard (osy) or grams per square meter (gsm), and the fiber diameters useful are usually expressed in microns. (Note that to convert from osy to gsm, multiply osy by 33.91.)

As used herein, the term "microfibers" means small diameter fibers having an average diameter not greater than about 75 microns, for example, having an average diameter of from about 0.5 microns to about 50 microns, or more particularly, having an average diameter of from about 2 microns to about 40 microns. Another frequently used expression of fiber diameter is denier, which is defined as grams per 9,000 meters of a fiber, and may be calculated as fiber diameter in microns squared, multiplied by the density in grams/cc, multiplied by 0.00707. A lower denier indicates a finer fiber and a higher denier indicates a thicker or heavier fiber. For example, a diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States, the unit of measurement is more commonly the "tex", which is defined as the grams per kilometer of fiber. Tex may be calculated as denier/9.

As used herein, the term "spunbonded fibers" refers to small diameter fibers which are formed by extruding molten thermoplastic material as filaments from a plurality of fine, usually circular capillaries of a spinnerette with the diameter of the extruded filaments then being rapidly reduced as taught, for example, by U.S. Pat. Nos. 4,340,563 to Appel et al., 3,692,618 to Dorschner et al., 3,802,817 to Matsuki et al., 3,338,992 and 3,341,394 to Kinney, 3,502,763 to Hartmann, 3,502,538 to Levy, and 3,542,615 to Dobo et al. Spunbond fibers are quenched and generally not tacky when they are deposited onto a collecting surface. Spunbond fibers are generally continuous and have average diameters larger than 7 microns, more particularly, between about 10 and 20 microns.

As used herein, the term "meltblown fibers" means fibers formed by extruding a molten thermoplastic material through a plurality of fine, usually circular, die capillaries as molten threads or filaments into converging high velocity gas (for example, airstreams) which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin. Meltblown fibers are microfibers which may be continuous or discontinuous, are generally smaller than 10 microns in average diameter, and are generally tacky when deposited onto a collecting surface.

As used herein, the term "polymer" generally includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, atactic and random symmetries.

As used herein, the term "personal care product" means diapers, training pants, absorbent underpants, adult incontinence products, and feminine hygiene products.

As used herein, the term "hydrophilic" means that the polymeric material has a surface free energy such that the polymeric material is wettable by an aqueous medium, that is, a liquid medium of which water is a major component. That is, an aqueous medium wets the nonwoven fabric that has been treated from a surfactant bath. The surfactant bath is made from at least 0.1% by weight of surfactant or surfactant mixtures and of no more than about 99.9% solvent, such as water, for example.

A coform material suitable for use in this invention is a nonwoven fabric-like material having a unique combination of strength, absorbency and hand comprising an air-formed matrix of thermoplastic polymer microfibers having an average fiber diameter of less than about 10 microns, and a multiplicity of individualized wood pulp fibers disposed throughout the matrix of microfibers and engaging at least some of the microfibers to space the microfibers apart from each other. The ratio of pulp fibers/microfibers is preferably in the range of about 10/90 to about 90/10, respectively. Thermoplastic polymers suitable for use in the coform material of this invention include polyolefins, for example, polyethylene, polypropylene, polybutylene and the like, polyamides, and polyesters. In accordance with a particularly preferred embodiment of this invention, the thermoplastic polymer used in the formation of the synthetic fibers of the coform material of this invention is polypropylene. The wood pulp fibers are interconnected by and held captive within the matrix of microfibers by mechanical entanglement of the microfibers with the wood pulp fibers, the mechanical entanglement and interconnection of the microfibers and wood pulp fibers alone forming a coherent integrated fiber structure. The coherent integrated fiber structure may be formed by the microfibers and wood pulp fibers without any adhesive, molecular or hydrogen bonds between the two different types of fibers. The wood pulp fibers are preferably distributed uniformly throughout the matrix of microfibers to provide a homogeneous material. The material is formed by initially forming a primary air stream containing the meltblown microfibers, forming a secondary air stream containing the wood pulp fibers, merging the primary and secondary streams under turbulent conditions to form an integrated air stream containing a thorough mixture of the microfibers and wood pulp fibers, and then directing the integrated air stream onto a forming surface to air form the fabric-like material. The microfibers are in a soft nascent condition at an elevated temperature when they are turbulently mixed with the wood pulp fibers in air.

In accordance with one preferred embodiment of this invention, the coform material is laminated with a secondary nonwoven fabric, for example, a spunbond liner.

In order to provide the coform material with improved fluid handling performance in accordance with this invention, the meltblown fibers are sprayed with a surfactant treatment system comprising a compound selected from the group consisting of ethoxylated hydrogenated fatty oils, monosaccharides, monosaccharide derivatives, polysaccharides, polysaccharide derivatives, and combinations thereof.

In accordance with a particularly preferred embodiment of this invention, the meltblown fibers are sprayed with AHCOVEL Base N-62, a blend of hydrogenated ethoxylated castor oil and sorbitan monooleate, the chemical formulas for which are as follows:

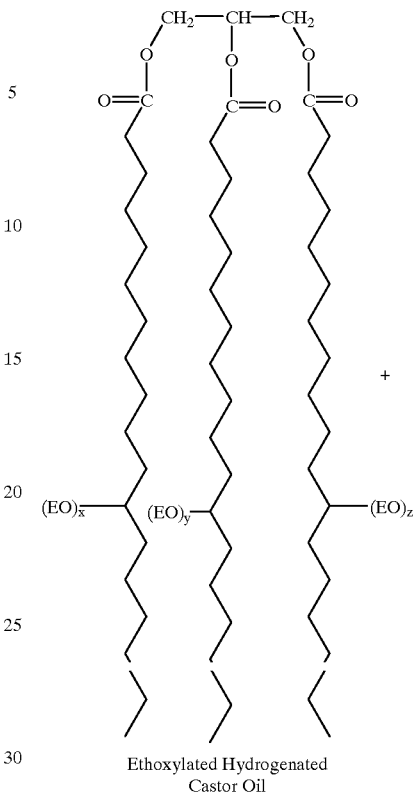

Ethoxylated Hydrogenated Castor Oil

+

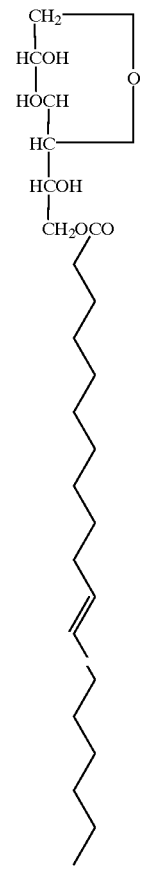

Sorbitan Monooleate x + y + z = 25

-continued available from Hodgson Textile Chemicals, Mount Holly, N.C.

In accordance with another preferred embodiment, the secondary nonwoven fabric is also treated with a surfactant treatment system preferably comprising AHCOVEL Base N-62 or a blend of AHCOVEL Base N-62 and GLUCOPON 220 UP, a mixture of alkyl polyglycosides having 8–10 carbons in the alkyl chain. For treatment of the coform material, the surfactant treatment system has a relatively low solids content, typically about 3% AHCOVEL. For treatment of the secondary nonwoven fabric, the surfactant treatment system has a relatively high solids content, typically greater than about 10%.

At high solids content, AHCOVEL Base N-62 is very viscous and difficult to apply using conventional treating methods. Traditional viscosity modification additives or surfactant blends may reduce the viscosity of this treatment, but they adversely affect the durability of the treated fabric. Accordingly, in accordance with one particularly preferred embodiment of this invention, the surfactant treatment system applied to the meltblown fibers further comprises an alkyl polyglycoside which not only reduces the viscosity of the AHCOVEL Base N-62 treatment, but also maintains the desired fabric durability. For best results, the alkyl polyglycoside is one having 8 to 10 carbons in the alkyl chain and is provided in an amount of about 5% to about 50%, preferably about 6% to about 40%, based upon the total surfactant composition weight. In accordance with one particularly preferred embodiment of this invention, the allyl polyglycoside is GLUCOPON 220 UP, which comprises an octylpolyglycoside, the chemical formula for which is as follows:

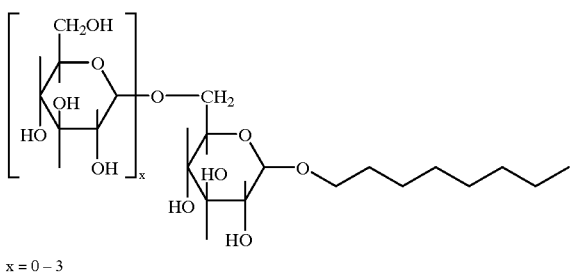

x = 0 – 3 available from Henkel Corporation, Ambler, Pa. Thus, the preferred surfactant treatment system for application to a coform material in accordance with this invention is a blend of AHCOVEL Base N-62 and GLUCOPON 220 UP (A/G) at ratios ranging from 1:1 to 20:1, respectively.

Table 1 below illustrates the effect on viscosity of AHCOVEL Base N-62 of the addition of GLUCOPON 220 UP, a solution of 60% alkyl polyglycoside in 40% water by weight. Viscosity determinations were made on 20% overall solid compositions and at a shear rate of 20 (1/sec) using a Viscometer: Brookfield DVII+, Spindle CP41 in each case.

TABLE 1

Effect of GLUCOPON on Viscosity* of AHCOVEL at 20% Solids

| Treating Composition | Ratio | Viscosity (cp.) | Temp. (c) | Shear Rate (sec.$^{-1}$) |
|---|---|---|---|---|
| Ahcovel | 1 | 1103 | 25 | 20 |
| Ahcovel | 1 | 150 | 47 | 20 |
| Ahcovel/Glucopon | 20/1 | 40 | 25 | 20 |
| Ahcovel/Glucopon | 15/1 | 14 | 25 | 20 |
| Ahcovel/Glucopon | 10/1 | <12.3 | 25 | 20 |
| Ahcovel/Glucopon | 5/1 | <12.3 | 25 | 20 |
| Ahcovel/Glucopon | 3/1 | <12.3 | 25 | 20 |
| Ahcovel/Glucopon | 1/1 | <12.3 | 25 | 20 |

*Measurements with Brookfield DVII + viscometer, spindle CP-41

For purposes of this invention, achieving a viscosity of less than about 100 cp under application conditions, preferably room temperature, is desirable so that high solids conventional application systems and procedures can be employed, such as the WEKO Rotor Dampening System available from WEKO. Other systems, such as brushed spray applicators and coating and printing applicators, may be used as will be apparent to those skilled in the art. As shown above, AHCOVEL by itself at high solids content fails to meet this requirement, but as little as one part in 20 of the addition of an alkyl polyglycoside, such as GLUCOPON 220 UP, reduces its viscosity dramatically.

Numerous methods for hydrophilic treatment of nonwoven materials with surfactants having low solids content are known and are commonly used. However, due to the high solvent content, a drying step is required. It is known that the heat effects of the drying process negatively impact the mechanical properties of nonwoven materials following surfactant treatment. Thus, the use of a high-solids content treatment system, at least about 10% solids and advantageously at least about 20% solids, minimizes or alleviates the need for drying, thereby retaining the inherent tensile strength of the fabric. Other obvious advantages of a high-solids treatment system include lower cost for surfactant formulation, shipping and storage, conserved energy and lower treatment cost, and better treatment uniformity.

In accordance with one preferred embodiment of this invention, the surfactant composition is applied to the meltblown and secondary nonwoven (spunbond) fibers at an add-on level ranging from about 0.1% to about 5% by weight. We have found that above about 5%, no additional benefit is obtained.

In accordance with one embodiment of this invention, the surfactant treatment system incorporates not only multiple surfactants for improved wettability with aqueous fluids, for example menstrual fluid, or for facilitating management of other bodily fluids (blood, urine, feces, etc.), but also include superabsorbents, bioactive compounds and macromolecules which may afford biofunctional attributes to the coform material of this invention, for example antibacterial activity, preservatives, anti-inflammatory, odor control, skin wellness, and the like.

The coform material in accordance with this invention preferably has a basis weight in the range of about 50 gsm to about 500 gsm and has a pulp/polymer ratio in the range of about 10/90 to about 90/10, respectively. The composition of the coform material can be varied within this range to provide the desired material absorbency and material integrity, the pulp being used for its absorbent properties and the polymer providing structural integrity.

Figure 2:
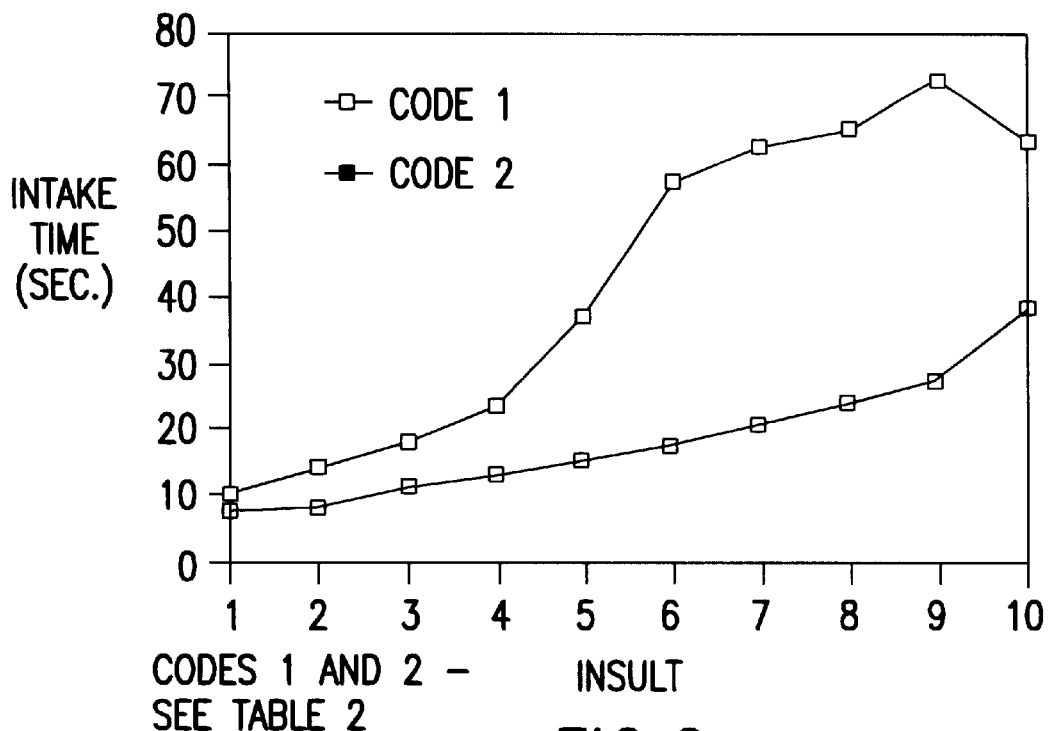
FIG. 2 is a diagram showing a comparison of a coform material treated with a surfactant in accordance with this invention compared to a known surfactant.
Figure 3:
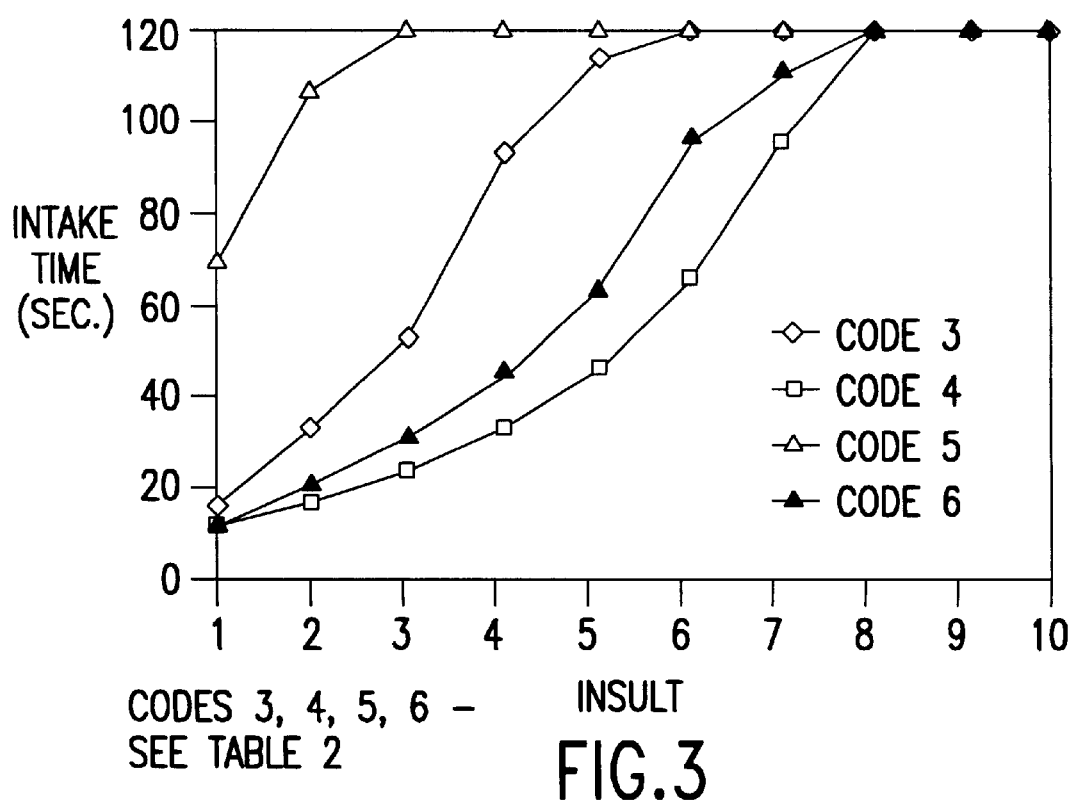
FIG. 3 is a diagram showing intake time for a second coform material coated with the surfactant of this invention compared to known surfactants.

FIGS. 2 and 3 show the effectiveness of a coform material in accordance with this invention in terms of fluid intake time (absorbency) compared to a coform material treated with a known surfactant treatment system, Triton X-102 from Union Carbide, as measured by the multiple insult drop test (MIDOT). The MIDOT test determines the time, in seconds, required for a material to absorb a specified amount of synthetic menstrual fluid. In the MIDOT test, a fabric to be tested, such as the coform material of this invention, is placed on a polycarbonate base. A middle cover plate is placed over the material and a cover plate with two designated open areas is placed on top of the middle cover plate. A specified amount of synthetic menstrual fluid is dispensed from a pump into the cover plate while simultaneously starting a stopwatch. The stopwatch is stopped when the meniscus of the fluid is no longer visually on the top of the cover material.

Table 2 summarizes the materials and treatment chemistry utilized in evaluation of the coform material of this invention. The material, as shown in Table 2 is a coform material treated with various surfactant treatment systems to which is laminated a spunbond web.

TABLE 2

| Product | Code | Spunbond surfactant | wt % | Coform surfactant | wt % |
|---|---|---|---|---|---|
| "A" | 1 | TRITON | 0.08 | TRITON | 0.4 |
|  | 2 | AHCOVEL | 0.3 | AHCOVEL | 0.4 |
| "B" | 3 | TRITON | 0.08 | TRITON | 0.4 |
|  | 4 | AHCOVEL | 0.3 | AHCOVEL | 0.4 |
|  | 5 | AG | 0.3 | AG | 0.4 |
|  | 6 | none | 0 | none | 0 |

"Triton" is Triton X-102 from Union Carbide.
"Ahcovel" is Ahcovel Base N-62 from Hodgson Textile Chemicals.
"AG" is a blend of Ahcovel Base N-62 and Glucopon 220 UP.
"Glucopon" is from Henkel Corp.

FIG. 2 shows a comparison of the material designated as product "A" treated with TRITON X-102 and AHCOVEL. As shown, the material treated with AHCOVEL exhibits the lowest intake time, that is faster absorbency, and better durability on multiple insults or multiple fluid exposure than the material treated with TRITON.

FIG. 3 is a similar plot for a product material designated "B" treated with TRITON X-102, AHCOVEL, a blend of AHCOVEL and GLUCOPON 220 UP, and no surfactant treatment at all. The data show that the material treated with AHCOVEL exhibits the fastest absorbency, that is the lowest intake time, and the material treated with a blend of AHCOVEl and GLUCOPON exhibits the second fastest absorbency. In both instances, durability on multiple insults is better than for the material treated with TRITON X-102.

A method for producing an integrated composite material in accordance with this invention comprises forming a plurality of synthetic fibers, forming a plurality of natural fibers, mixing the synthetic fibers and the natural fibers and depositing the mixture onto a forming surface, thereby forming an integrated composite material layer, and applying a surfactant treatment system, preferably using a spray system such as a Spray Boom, comprising a compound selected from the group consisting of ethoxylated hydrogenated fatty oils, monosaccharides, monosaccharide derivatives, polysaccharides, polysaccharide derivatives, and combinations thereof at least to the plurality of synthetic fibers. In accordance with one particularly preferred embodiment, the synthetic fibers are produced by a meltblown process. It will be apparent to those skilled in the art that application of the surfactant treatment to the synthetic fibers may be before, during or after formation of the integrated composite material layer.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An integrated composite material suitable for use in a personal care absorbent article comprising:
   a matrix of synthetic fibers;
   a plurality of natural fibers disposed throughout said matrix of synthetic fibers; and
   a surfactant treatment system comprising a mixture of alkyl polyglycosides having 8–10 carbons in the alkyl chain.

2. A material in accordance with claim 1, wherein one of said alkyl polyglycosides is octyl polyglycoside.

3. A material in accordance with claim 1, wherein said surfactant treatment system further comprises a blend of ethoxylated hydrogenated castor oil and sorbitan monooleate.

4. A material in accordance with claim 3, wherein a ratio of said blend of ethoxylated hydrogenated castor oil and sorbitan monooleate to said mixture of alkyl polyglycosides is in a range of about 1:1 to about 20:1.

5. A material in accordance with claim 1, wherein said synthetic fibers are meltblown fibers.

6. A material in accordance with claim 5, wherein said meltblown fibers are made from polypropylene.

7. A material in accordance with claim 1, wherein said natural fibers are pulp fibers.

8. A material in accordance with claim 1, wherein said synthetic fibers are polypropylene meltblown fibers and said natural fibers are pulp fibers.

9. A material in accordance with claim 1 further comprising a secondary nonwoven material laminated thereto.

10. A material in accordance with claim 9, wherein said secondary nonwoven material is treated with said surfactant treatment system at an add-on level in a range of about 0.1 to about 5.0% by weight.

11. A material in accordance with claim 1, wherein said surfactant treatment system is applied at an add-on level in a range of about 0.1 to 5.0% by weight.

12. A material in accordance with claim 1, wherein said surfactant treatment system is applied to said natural fibers.

13. A material in accordance with claim 1, wherein a basis weight of said material is in a range of about 50 gsm to about 500 gsm.

14. A material in accordance with claim 1, wherein a ratio of said natural fibers to said synthetic fibers is in a range of about 10/90 to about 90/10, respectively.

15. An integrated composite material in accordance with claim 1, wherein a solids content of said surfactant treatment system is at least about 10%.

16. An integrated composite material comprising:
   a matrix of synthetic fibers;
   a plurality of natural fibers disposed throughout said matrix of synthetic fibers; and
   a surfactant treatment system comprising a mixture of alkyl polyglycosides having 8–10 carbons in the alkyl chain applied at an add-on level in a range of about 0.1 to 5.0% by weight.

* * * * *